(12) United States Patent
Hofschneider et al.

(10) Patent No.: US 6,623,951 B1
(45) Date of Patent: Sep. 23, 2003

(54) HBV VECTORS AND CELLS FOR PRODUCING THE SAME

(75) Inventors: Peter Hofschneider, München (DE); Peter Habenberger, München (DE); Ludwig Weiss, Kissing (DE)

(73) Assignee: MondoGen GmbH, Martinsried (DE)

( * ) Notice: Subject to any disclaimer, the term of this patent is extended or adjusted under 35 U.S.C. 154(b) by 0 days.

(21) Appl. No.: 08/952,674

(22) PCT Filed: May 9, 1996

(86) PCT No.: PCT/DE96/00807

§ 371 (c)(1),
(2), (4) Date: Mar. 2, 1998

(87) PCT Pub. No.: WO96/35797

PCT Pub. Date: Nov. 14, 1996

(30) Foreign Application Priority Data

May 12, 1995 (DE) .......................... 195 17 532

(51) Int. Cl.$^7$ .......................... C12N 15/00; C12N 7/00; C12N 15/63; C12N 15/85
(52) U.S. Cl. .............. 435/235.1; 435/320.1; 435/440; 435/455
(58) Field of Search .......................... 435/235.1, 320.1, 435/440, 455; 514/44

(56) References Cited

U.S. PATENT DOCUMENTS 5,981,274 A   11/1999   Tyrrell et al.

FOREIGN PATENT DOCUMENTS

| EP | WO90/02176 | 3/1990 |
| EP | WO91/16420 | 10/1991 |

OTHER PUBLICATIONS

Bartenschlager et. al.; Hepadnaviral assembly is initiated by polymerase binding to the encapsidation signal in viral RNA genome, 1992, The EMBO Journal vol. 11, No. 9: 3413–3420.*

Alka et. al., Hepatitis B Virus Surface (S) Transactivator With DNA–Binding Properties; 2000; JOurnal of Medical Virloogy 61:1–10.*

Ori et. al., Hepaitis B virus Enhancer Biinds and is Activated by the Hepatocyte Nuclear Factor 3, 1995; Virology 207:98–106.*

Blum et. al., Hepatitis B Virus X Protein Is Not Central to the Viral Life Cycle In Vitro; 1992, Journal of Virology ,vol. 66. No., 2:1223–1227.*

Nakatake et. al., Effect of X Protein on Transactivation of Hepatitis B Virus Promoters and on Vrral Replication, 1993; Virology 195:305–314.*

Horikita et al. Differences in the Entire Nucleotide Sequence Between Hepatitis B Virus Genomes from Carriers Positive for Antibody to Hepatitis B e Antigen with and without Active Disease. Journal of Medical Virolory. vol. 44, pp. 96–103, 1994.*

Verma et al. Gene therapy– Promises, Problems, and Prospects. Nature. vol. 389, pp. 239–242, Sep. 18, 1997.*

Medical Virology Fourth Edition. White et al., eds. Academic Press. pp. 358 and 366, 1994.*

Fujiyama, et al. "Cloning and Structural Analyses of Hepatitis B Virus DNAs, Subtype adr," Nucleic Acids Research, vol. 11 No. 13 (1983) pp. 4601–4610.

Graham, et al. "A New Technique for the Assay of Infectivity of Human Adenovirus 5 DNA," Virology 52, pp. 456–467.

Pollack, et al. "An RNA Stem–Loop Structure Directs Hepatitis B Virus Genomic RNA Encapsidation," Journal of Virology, Jun. 1993, vol. 67, No. 6, pp. 3254–3263.

Knowles, et al. "Human Hepatocellular Carcinoma Cell Lines Secrete the Major Plasma Proteins and Hepatitis B Surface Antigen," Science, vol. 209, Jul. 25, 1980, pp. 497–499.

McCutchan, et al. "Enhancement of the Infectivity of Simian Virus 40 Deoxyribonucleic Acid with Diethylaminoethyl-Dextran[1,2]," Journal of the National Cancer Institute, vol. 41, No. 2, Aug. 1968, pp. 351–357.

Sugata, et al. "Analysis of the X Gene Promoter of Woodchuck Hepatitis Virus," Virology 205 (1994) pp. 314–320.

Uchida, et al. "Complete Nucleotide Sequences and the Characteristics of Two Hepatitis B Virus Mutants Causing Serologically Negative Acute or Chronic Hepatitis B," Journal of Medical Virology 45, (1995), pp. 247–252.

* cited by examiner

Primary Examiner—Deborah Crouch
Assistant Examiner—Joseph Woitach
(74) Attorney, Agent, or Firm—Marianne Fuierer; Steven J. Hultquist; Yongzhi Yang

(57) ABSTRACT

This invention relates to an HBV vector in which functional genes of HBV are at least partially deleted. In addition, this invention concerns a process for producing such an HBV vector as well as cells usable for this purpose.

5 Claims, 8 Drawing Sheets

```
  1  TATAGTGTCA CCTAAATCGT ATGTGTATGA TACATAAGGT TATGTATTAA
 51  TTGTAGCCGC GTTCTAACGA CAATATCTAC AAGCCTAATT GTGTAGCATC
101  TGGCTTACTG AAGCAGACCC TATCATCTCT CTCGTAAACT GCCGTCAGAG
151  TCGGTTTGGT TGGACGAACC TTCTGAGTTT CTGGTAACGC CGTCCCGCAC
201  CCGGAAATGG TCAGCGAACC AATCAGCAGG GTCATCGCTA GCCAGATCCT
251  CTACGCCCGA CGCATCGTGG CCGGCATCAC CGGGCCACA GGTGCGGTTG
301  CTGGCGCCTA TATCGCCCGAC ATCACCGATG GGGAAGATCG GGCTCGCCAC
351  TTCGGGCTCA TGAGCGCTTG TTTCGGCGTG GGTATGGTGG CAGGCCCGTG
401  GCCGGGGGAC TGTTGGGCGC CATCTCCTTG CATGCACCAT TCCTTGCGGC
451  GGCGGTGCTC AACGGCCTCA ACCTACTACT GGGCTGCTTC CTAATGCAGG
501  AGTCGCATAA GGGAGAGCGT CGATATGGTG CACTCTCAGT ACAATCTGCT
551  CTGATGCCGC ATAGTTAAGC CAGCCCCGAC ACCGCCAAC ACCCGCTGAC
```

Figure 1A

```
601   GCGCCCTGAC GGGCTTGTCT GCTCCCGGCA TCCGCTTACA GACAAGCTGT
651   GACCGTCTCC GGGAGCTGCA TGTGTCAGAG GTTTTCACCG TCATCACCGA
701   AACGGCGAG ACGAAAGGGC CTCGTGATAC GCCTATTTTT ATAGGTTAAT
751   GTCATGATAA TAATGGTTTC TTAGACGTCA GGTGGCACTT TCGGGGAAA
801   TGTGCGCGGA ACCCCTATTT GTTTATTTTT CTAAATACAT TCAAATATGT
851   ATCCGCTCAT GAGACAATAA CCCTGATAAA TGCTTCAATA ATATTGAAAA
901   AGGAAGAGTA TGAGTATTCA ACATTTCCGT GTCGCCCTTA TTCCCTTTTT
951   TGCGGCATTT TGCCTTCCTG TTTTTGCTCA CCCAGAAACG CTGGTGAAAG
1001  TAAAAGATGC TGAAGATCAG TTGGGTGCAC GAGTGGGTTA CATCGAACTG
1051  GATCTCAACA GCGGTAAGAT CCTTGAGAGT TTTCGCCCCG AAGAACGTTT
1101  TCCAATGATG AGCACTTTTA AAGTTCTGCT ATGTGGCGCG GTATTATCCC
1151  GTATTGACGC CGGGCAAGAG CAACTCGGTC GCCGCATACA CTATTCTCAG
```

Figure 1B

```
1201  AATGACTTGG TTGAGTACTC ACCAGTCACA GAAAAGCATC TTACGGATGG
1251  CATGACAGTA AGAGAATTAT GCAGTGCTGC CATAACCATG AGTGATAACA
1301  CTGCGGCCAA CTTACTTCTG ACAACGATCG GAGGACCGAA GGAGCTAACC
1351  GCTTTTTTGC ACAACATGGG GGATCATGTA ACTCGCCTTG ATCGTTGGGA
1401  ACCGGAGCTG AATGAAGCCA TACCAAACGA CGAGCGTGAC ACCACGATGC
1451  CTGTAGCAAT GGCAACAACG TTGCGCAAAC TATTAACTGG CGAACTACTT
1501  ACTCTAGCTT CCCGGCAACA ATTAATAGAC TGGATGGAGG CGGATAAAGT
1551  TGCAGGACCA CTTCTGCGCT CGGCCCTTCC GGCTGGCTGG TTTATTGCTG
1601  ATAAATCTGG AGCCGGTGAG CGTGGGTCTC GCGGTATCAT TGCAGCACTG
1651  GGGCCAGATG GTAAGCCCTC CCGTATCGTA GTTATCTACA CGACGGGGAG
1701  TCAGGCAACT ATGGATGAAC GAAATAGACA GATCGCTGAG ATAGGTGCCT
1751  CACTGATTAA GCATTGGTAA CTGTCAGACC AAGTTTACTC ATATATACTT
```

Figure 1C

```
1801  TAGATTGATT TAAAACTTCA TTTTTAATTT AAAAGGATCT AGGTGAAGAT
1851  CCTTTTTGAT AATCTCATGA CCAAAATCCC TTAACGTGAG TTTTCGTTCC
1901  ACTGAGCGTC AGACCCCGTA GAAAAGATCA AAGGATCTTC TTGAGATCCT
1951  TTTTTTCTGC GCGTAATCTG CTGCTTGCAA ACAAAAAAAC CACCGCTACC
2001  AGCGGTGGTT TGTTTGCCGG ATCAAGAGCT ACCAACTCTT TTTCCGAAGG
2051  TAACTGGCTT CAGCAGAGCG CAGATACCAA ATACTGTCCT TCTAGTGTAG
2101  CCGTAGTTAG GCCACCACTT CAAGAACTCT GTAGCACCGC CTACATACCT
2151  CGCTCTGCTA ATCCTGTTAC CAGTGGCTGC TGCCAGTGGC GATAAGTCGT
2201  GTCTTACCGG GTTGGACTCA AGACGATAGT TACCGGATAA GGCGCAGCGG
2251  TCGGGCTGAA CGGGGGGTTC GTGCACACAG CCCAGCTTGG AGCGAACGAC
2301  CTACACCGAA CTGAGATACC TACAGCGTGA GCATTGAGAA AGCGCCACGC
2351  TTCCCGAAGG GAGAAAGGCG GACAGGTATC CGGTAAGCGG CAGGGTCGGA
```

Figure 1D

```
2401  ACAGGAGAGC GCACGAGGGA GCTTCCAGGG GGAAACGCCT GGTATCTTTA
2451  TAGTCCTGTC GGGTTTCGCC ACCTCTGACT TGAGCGTCGA TTTTTGTGAT
2501  GCTCGTCAGG GGGGCGGAGC CTATGGAAAA ACGCCAGCAA CGCGGCCTTT
2551  TTACGGTTCC TGGCCTTTTG CTGGCCTTTT GCTCACATGT TCTTTCCTGC
2601  GTTATCCCCT GATTCTGTGG ATAACCGTAT TACCGCCTTT GAGTGAGCTG
2651  ATACCGCTCG CCGCAGCCGA ACGACCGAGC GCAGCGAGTC AGTGAGCGAG
2701  GAAGCGGAAG AGCGCCTGAT GCGGTATTTT CTCCTTACGC ATCTGTGCGG
2751  TATTTCACAC CGCATATGGT GCACTCTCAG TACAATCTGC TCTGATGCCG
2801  CATAGTTAAG CCAGTATACA CACTCCGCTA TCGCTACGTG ACTGGGTCAT
2851  GGCTGCGCCC CGACACCCGC CAACACCCGC TGACGCGCCC TGACGGGCTT
2901  GTCTGCTCCC GGCATCCGCT TACAGACAAG CTGTGACCGT CTCCGGGAGC
2951  TGCATGTGTC AGAGGTTTTC ACCGTCATCA CCGAAACGCG CGAGGCCCAG
3001
```

Figure 1E

| | |
|---|---|
| 3051 | CTGGCTTATC GAAATTAATA CGACTCACTA TAGGGAGACC CAAGCTTGCA |
| 3101 | TGCCTGCAGG TCGACTCTAG AGGATCCTGC GCGGGACGTC CTTTGTCTAC |
| 3151 | GTCCCGTCGG CGCTGAATCC CGCGGACGAC CCGTCTCGGG GCCGTTTGGG |
| 3201 | ACTCTACCGT CCCCTTCTTC ATCTGCCGTT CCGGCCGACC ACGGGGCGCA |
| 3251 | CCTCTCTTTA CGCGGTCTCC CCGTCTGTGC CTTCTCATCT GCCGGTCCGT |
| 3301 | GTGCACTTCG CTTCACCTCT GCACGTCGCA TGGAGACCAC CGTGAACGCC |
| 3351 | CACCAGGTCT TGCCCAAGGT CTTACATAAG AGGACTCTTG GACTCTCAGC |
| 3401 | GATGTCAACG ACCGACCTTG AGGCATACTT CAAAGACTGT TTGTTTAAGG |
| 3451 | ACTGGGAGGA GTTGGGGGAG GAGATTAGGT TAAAGGTCTT TGTACTAGGA |
| 3501 | GGCTGTAGGC ATAAATTGGT CTGTTCACCA GCACCATGCA ACTTTTTCAC |
| 3551 | CTCTGCCTAA TCATCTCATG TTCATGTCCT ACTGTTCAAG CCTCCAAGCT |
| 3601 | GTGCCTTGGG TGGCTTTGGG GCATGGACAT TGACCCGTAT AAAGAATTTG |

Figure 1F

| | |
|---|---|
| 3651 | GAGCTTCTGT GGAGTTACTC TCTTTTTGC CTTCTGACTT CTTCCTTCT |
| 3701 | ATTCGAGATC TCCTCGACAC CGCCTCAGCT CTATATCGGG AGGCCTGCGG |
| 3751 | CCGCTCGAGT TAACTAGTCG CGATGCATCG ATGATCACCC GGGCCATGGC |
| 3801 | TGCTAGGGTG TGCTGCCAAC TGGATCCTGC GCGGGACGTC CTTGTCTAC |
| 3851 | GTCCCGTCGG CGCTGAATCC CGGGACGAC CCGTCTCGGG GCCGTTTGGG |
| 3901 | ACTCTACCGT CCCCTCTTC ATCTGCCGTT CCGGCCGACC ACGGGGCGCA |
| 3951 | CCTCTCTTTA CGCGGTCTCC CCGTCTGTGC CTTCTCATCT GCCGGTCCGT |
| 4001 | GTGCACTTCG CTTCACCTCT GCACGTCGCA TGGAGACCAC CGTGAACGCC |
| 4051 | CACCAGGTCT TGCCCAAGGT CTTACATAAG AGGACTCTTG GACTCTCAGC |
| 4101 | GATGTCAACG ACCGACCTTG AGGCATACTT CAAAGACTGT TTGTTTAAGG |
| 4151 | ACTGGGAGGA GTTGGGGGAG GAGATTAGGT TAAAGGTCTT TGTACTAGGA |
| 4201 | GGCTGTAGGC ATAAATTGGT CTGTTCACCA GCACCATGCA ACTTTTTCAC |

Figure 1G

| | |
|---|---|
| 4251 | CTCTGCCTAA TCATCTCATG TTCATGTCCT ACTGTTCAAG CCTCCAAGCT |
| 4301 | GTGCCTTGGG TGGCTTTGGG GCATGGACAT TGACCCGTAT AAAGAATTTG |
| 4351 | GAGCTTCTGT GGAGTTACTC TCTTTTTGC CTTCTGACTT CTTCCTTCT |
| 4401 | ATTCGAGATC TCCTCGACAC CGCCTCAGCT CTATATCGGG AGGGGGTACC |
| 4451 | GAGCTCGAAT TCCGTGTATT C |

Figure 1H

HBV VECTORS AND CELLS FOR PRODUCING THE SAME

HBV Vectors and Cells for Producing the Same This invention relates to HBV vectors, processes for the provision thereof and cells usable for this purpose as well as the use of the HBV vectors.

Efficient methods are required for a gene therapy to transfer a "therapeutic" DNA into select target organs. Up to the present, retroviral vectors have been used above all for this purpose. However, they have the drawback that the cells to be treated first have to be propagated in vitro, infected and then be transferred into the patient again. However, it should be the objective of a gene therapy to treat cells in situ.

For an in vivo gene therapy the strict organ specificity of the employed vector system is an absolute precondition. The hepatocytes of the liver are of special interest for this purpose. The liver is the source of most of the serum proteins and plays a central part for the regulation of the metabolism in the peripheral organs. Therefore, a plurality of different, inherited metabolic defects manifest themselves in the liver. In addition, the liver is also affected in the case of some viral infections which can be treated only very poorly. Furthermore, the liver could be used as a bioreactor for the secretion of diverse proteins, provided that a suitable gene transfer system existed. Thus, new paths could be trodden also for the treatment of diseases which do not manifest themselves in the liver.

However, a liver cell-specific gene transfer system for which an in vivo application could be in consideration does not yet exist.

Therefore, it is the object of the present invention to provide a gene transfer system which is liver cell-specific and suitable for an in vivo gene therapy.

According to the invention this is achieved by the subject matters in the claims.

Therefore, the subject matter of the present invention relates to a HBV vector in which functional genes of HBV are at least partially deleted.

The expression "HBV" refers to hepatitis B virus. This is a DNA virus having a genome length of 3.2 kb. The genome of hepatitis B virus contains four partially overlapping open reading frames (ORF): the pol-ORF (HBV polymerase), the S-ORFs (surface proteins), the C-ORFs (capsid proteins) and the X-ORF (viral transactivator) Hepatitis B virus is liver cell-specific.

The expression "HBV vector" comprises any HBV vector which is suitable for a gene transfer, especially in a gene therapy, most especially in an in vivo gene therapy. In this connection, the expression "vector" relates to a DNA molecule as well as a virus particle.

The expression "in which functional genes of HBV are at least partially deleted" refers to the fact that in an HBV vector according to the invention one to all genes necessary for the replication of HBV are partially or fully deleted. Such genes are especially those which code for polymerase, the surface proteins and the capsid proteins of HBV. Because of the above deletion, an HBV vector according to the invention can no longer replicate independently in a eukaryotic cell.

It is advantageous when in an HBV vector according to the invention the genes for the polymerase, the surface proteins and the capsid proteins of HBV are at least partially deleted. It is especially advantageous when these genes are fully deleted.

Furthermore, it is of advantage when in an HBV vector according to the invention the gene of the transactivator of HBV is also mutated or partially deleted and fully deleted, respectively.

A preferred HBV vector of the present invention is pHBV/V1. Its DNA sequence is indicated in FIG. 1. In pHBV/V1, the genes for the polymerase, the surface proteins and the capsid proteins of HBV are fully deleted. Likewise, the gene for the transactivator of HBV has an ochre mutation. pHBV/V1 was deposited with the DSM (Deutsche Sammlung von Mikroorganismen und Zellkulturen GmbH [German-type collection of micro-organisms and cell cultures]Mascheroder Weg 1b, D-38124 Braunschweig, Germany) under DSM 9947 on May 3, 1995.

Because of its deletion, an exogeneous or foreign or heterologous DNA can be inserted in an HBV vector according to the invention, and it can then be expressed in the cells accommodating the HBV vector. A foreign DNA may be any DNA, particularly a diagnostically and/or therapeutically effective gene. The length of the foreign DNA may vary, it being advantageous when it does not exceed about 3 kb. On a protein basis, this length corresponds to a molecular weight of over 100,000, which is quite sufficient for gene-therapeutic applications.

A foreign DNA is inserted in an HBV vector according to the invention via the "multiple cloning site" of the latter. Hence it is also possible to insert the foreign DNA between two inverse terminal repetitions of adeno-associated viruses. This would increase the integration frequency as well as the integration specificity of the foreign DNA in a special chromosome.

Another subject matter of the present invention relates to a process for producing the above HBV vectors. In such a process, the defect in the independent replication of an HBV vector according to the invention is overcome by transfecting it into cells which express functional HBV proteins. The expression of the HBV proteins can be transient and/or stable, a stable expression being preferred. HBV vectors are provided as DNA molecules as well as virus particles by the process according to the invention.

Common methods can be used for producing the above cells. It is favorable to transfect hepatoma cells, e.g. Hep G2 cells (cf. Knowles, B. B. et al., Science 209 (1980), 497–499) with expression plasmids coding for functional HBV proteins. It is especially favorable when the genes for the individual functional HBV proteins are present on differing expression plasmids.

For the preparation of the above expression plasmids, it proves to be favorable to use common HBV vectors having selection markers and delete therein the epsilon region necessary for packaging as well as differing functional HBV genes. The DNA sequence of HBV, including the epsilon region, is known (cf. e.g. Fujiyama, A. et al., Nucl. Acids Res. 13, (1983), 4601–4610; Polack, J. R. and Ganem, D., J. Virol. 67, (1993), 3254–3263).

Common methods can be used for the transfection of hepatoma cells, e.g. Hep G2 cells, having the above expression plasmids. For example, a DEAE-dextran process (cf. McCutchan, J. H. and Pagano, J. S., J. Natl. Cancer Inst. 41, (1968), 351–357) is suitable for a transient expression of the functional HBV proteins, whereas e.g. a calcium phosphate precipitation process (cf. Graham, F. L. and van der Eb, A. J., Virology, 52 (1973), 456–467) has to be mentioned for a stable expression. Cells are obtained which express functional HBV proteins. Such cells also represent a subject matter of the present invention. Of these those are preferred which express the polymerase, the surface antigens and the capsid proteins of HBV, particularly express them in stable fashion.

The present invention serves for providing a gene transfer system which is liver cell-specific and suitable for a gene therapy, particularly an in vivo gene therapy. The gene transfer system comprises HBV vectors and cells in which these vectors can be provided.

The present invention enables to transfer foreign DNA into liver cells where it is expressed. Thus, it does not only open up possibilities of treating monogenic metabolic defects, e.g. familial hypercholesterolemia, hyperammonemia, hyperbilirubinemia, phenylketonuria, $\alpha_1$-antitrypsin deficiency, hemophilia, etc., but also of treating multifactorial diseases such as the virus hepatitises, e.g. HBV, HCV, HDV, and last but not least the primary liver cell carcinoma.

In addition, the present invention provides the possibility of using the liver as bioreactor for the secretion of any therapeutic proteins into the blood. This results in new aspects of gene therapy, which exceed by far the original target organ, such as the treatment of malignant diseases, of viral infections or generally of diseases which do not manifest themselves in the liver.

Moreover, by means of the present invention it is possible to monitor the most differing processes for killing viruses in body fluids withdrawn, e.g. blood. For this purpose, an HBV vector according to the invention, which is provided with a minotor gene, can be added to the body fluid before the process starts and then be determined at certain intervals.

Thus, the present invention is perfectly suited as a reagent for diagnosis and/or treatment.

BRIEF DESCRIPTION OF THE DRAWING

The FIGURE shows the DNA sequence of an HBV vector according to the invention, pHBV/V1. This DNA sequence comprises the following:

| Nucleotide No. | Elements |
|---|---|
| 3262–3272 | "direct repeat II" of HBV |
| 3496–3504 | "direct repeat I" of HBV |
| 3519–3579 | epsilon region of HBV |
| 3694–3748 | "multiple cloning site" |
| 3962–3970 | "direct repeat II" of HBV |
| 4196–4204 | "direct repeat I" of HBV |
| 4288–4293 | poly-A region |

The other nucleotides comprise those of the cloning vector pSPT 19 (cf. Example 1).

The following examples explain the invention.

EXAMPLE 1

Construction of an HBV Vector According to the Invention, pHBV/V1

A 621 bp long BamHI/Stu I fragment of adr 4 was cut out of the plasmid pBRHBadr4 (cf. Fujiyama, A. et al., above) which contains an HBV subtype, adr 4, and inserted in the cloning vector PSPT 19 opened by BamHI/Sma I (cf. catalog of Boehringer Mannheim, order No. 909815). The plasmid PSPT 0.2×HBV was obtained. This plasmid contains all regulatory elements of the $E_{11}/C_p$ region, which are necessary for the HBV replication. In pSPT 0.2×HBV, a complete 3215 bp long HBV genome (BamHI/BamHI fragment) of pBRHBadr4 (see above) was inserted at the BamHI restriction site. The plasmid pSPT 1.2×HBV was obtained. The above, regulatory elements of the $E_{11}/C_p$ region are present in this plasmid at the 5' end and also at the 3' end of the HBV portion. In addition, an ochre mutation in codon 8 was inserted in the X-ORF (see above) of pSPT 1.2×HBV. The plasmid PSPT 1.2×HBV Mx was obtained. This plasmid was cleaved with StuI and NcoI (restriction sites in the HBV genome) and the functional genes of HBV were removed. A "multiple cloning site" was inserted instead. An HBV vector according to the invention, pHBV/V1, was obtained.

EXAMPLE 2

Expression of a Foreign DNA in an HBV Vector According to the Invention, pHBV/V1

A known foreign DNA was inserted in the "multiple cloning site" of pHBV/V1 of Example 1. This was the luciferase gene and the LacZ gene fragment, respectively. In the former case, the plasmid pV1/HBV-Luc was obtained and, in the latter case, the plasmid pV1/HBV-LacZ was obtained. Both plasmids were used for a transient transfection of HepG2 cells (see above).

It showed that both foreign DNAs were expressed. This is also an evidence for the replication of pHBV/V1 in cells which produce HBV-WT particles.

What is claimed is:

1. A hepatitis B virus (HBV) vector comprising a modified HBV genome characterized by a mutated HBV-X-ORF rendering the HBV-X-ORF non-functional by virtue of a mutation in codon 8 of the HBV-X-ORF; and at least one deletion of pol-ORF, S-ORF and C-ORF which renders the HBV genome replication-defective.

2. A hepatitis B virus (HBV) vector comprising a modified HBV genome characterized by
   (i) an HBV-X-ORF including a modification rendering the HBV-X-ORF non-functional, wherein the modification is a partial deletion of the HBV-X-ORF; and
   (ii) a deletion of at least one of pol-ORF, S-ORF and C-ORF.

3. The HBV vector deposited on May 3, 1995 with Deutsche Sammlung von Mikroorganismen und Zelikulturen under accession number DSM 9947.

4. A hepatitis B virus (HBV) vector comprising a modified HBV genome characterized by (i) an HBV-X-ORF including a modification rendering the HBV-X-ORF non-functional, wherein the modification is a partial deletion of the HBV-X-ORF and (ii) a deleted pol-ORF, S-ORF and C-ORF open reading frames.

5. A hepatitis B virus (HBV) vector comprising a modified HBV genome including the following modifications:
   (a) a modification which renders nonfunctional the HBV-X-ORF, consisting of a mutation in codon 8 of HBV-X-ORF; and
   (b) deletions of the pol-ORF, S-ORF and C-ORF open reading frames.

* * * * *

SEQUENCE LISTING

```
<160> NUMBER OF SEQ ID NOS: 1

<210> SEQ ID NO 1
<211> LENGTH: 4421
<212> TYPE: DNA
<213> ORGANISM: Artificial Sequence
<220> FEATURE:
<223> OTHER INFORMATION: Description of Artificial Sequence: pHBV/V1

<400> SEQUENCE: 1
tatagtgtca cctaaatcgt atgtgtatga tacataaggt tatgtattaa ttgtagccgc      60
gttctaacga caatatctac aagcctaatt gtgtagcatc tggcttactg aagcagaccc     120
tatcatctct ctcgtaaact gccgtcagag tcggtttggt tggacgaacc ttctgagttt     180
ctggtaacgc cgtcccgcac ccggaaatgg tcagcgaacc aatcagcagg gtcatcgcta     240
gccagatcct ctacgccgga cgcatcgtgg ccggcatcac cggcgccaca ggtgcggttg     300
```

-continued

| | |
|---|---|
| ctggcgccta tatcgccgac atcaccgatg gggaagatcg ggctcgccac ttcgggctca | 360 |
| tgagcgcttg tttcggcgtg ggtatggtgg caggcccgtg gccggggggac tgttgggcgc | 420 |
| catctccttg catgcaccat tccttgcggc ggcggtgctc aacggcctca acctactact | 480 |
| gggctgcttc ctaatgcagg agtcgcataa gggagagcgt cgatatggtg cactctcagt | 540 |
| acaatctgct ctgatgccgc atagttaagc cagccccgac acccgccaac acccgctgac | 600 |
| gcgccctgac gggcttgtct gctcccggca tccgcttaca gacaagctgt gaccgtctcc | 660 |
| gggagctgca tgtgtcagag gttttcaccg tcatcaccga aacgcgcgag acgaaagggc | 720 |
| ctcgtgatac gcctattttt ataggttaat gtcatgataa taatggtttc ttagacgtca | 780 |
| ggtggcactt tcggggaaa tgtgcgcgga acccctattt gtttattttt ctaaatacat | 840 |
| tcaaatatgt atccgctcat gagacaataa ccctgataaa tgcttcaata atattgaaaa | 900 |
| aggaagagta tgagtattca acatttccgt gtcgccctta ttcccttttt tgcggcattt | 960 |
| tgccttcctg tttttgctca cccagaaacg ctggtgaaag taaaagatgc tgaagatcag | 1020 |
| ttgggtgcac gagtgggtta catcgaactg gatctcaaca gcggtaagat ccttgagagt | 1080 |
| tttcgccccg aagaacgttt tccaatgatg agcacttta aagttctgct atgtggcgcg | 1140 |
| gtattatccc gtattgacgc cgggcaagag caactcggtc gccgcataca ctattctcag | 1200 |
| aatgacttgg ttgagtactc accagtcaca gaaaagcatc ttacggatgg catgacagta | 1260 |
| agagaattat gcagtgctgc cataaccatg agtgataaca ctgcggccaa cttacttctg | 1320 |
| acaacgatcg gaggaccgaa ggagctaacc gcttttttgc acaacatggg gatcatgta | 1380 |
| actcgccttg atcgttggga accggagctg aatgaagcca taccaaacga cgagcgtgac | 1440 |
| accacgatgc ctgtagcaat ggcaacaacg ttgcgcaaac tattaactgg cgaactactt | 1500 |
| actctagctt cccggcaaca attaatagac tggatggagg cggataaagt tgcaggacca | 1560 |
| cttctgcgct cggcccttcc ggctggctgg tttattgctg ataaatctgg agccggtgag | 1620 |
| cgtgggtctc gcggtatcat tgcagcactg gggccagatg gtaagccctc ccgtatcgta | 1680 |
| gttatctaca cgacggggag tcaggcaact atggatgaac gaaatagaca gatcgctgag | 1740 |
| ataggtgcct cactgattaa gcattggtaa ctgtcagacc aagtttactc atatatactt | 1800 |
| tagattgatt taaaacttca ttttaattt aaaaggatct aggtgaagat cctttttgat | 1860 |
| aatctcatga ccaaaatccc ttaacgtgag ttttcgttcc actgagcgtc agaccccgta | 1920 |
| gaaaagatca aaggatcttc ttgagatcct ttttttctgc gcgtaatctg ctgcttgcaa | 1980 |
| acaaaaaaac caccgctacc agcggtggtt tgtttgccgg atcaagagct accaactctt | 2040 |
| tttccgaagg taactggctt cagcagagcg cagataccaa atactgtcct tctagtgtag | 2100 |
| ccgtagttag gccaccactt caagaactct gtagcaccgc ctacatacct cgctctgcta | 2160 |
| atcctgttac cagtggctgc tgccagtggc gataagtcgt gtcttaccgg gttggactca | 2220 |
| agacgatagt taccggataa ggcgcagcgg tcgggctgaa cggggggttc gtgcacacag | 2280 |
| cccagcttgg agcgaacgac ctacaccgaa ctgagatacc tacagcgtga gcattgagaa | 2340 |
| agcgccacgc ttcccgaagg gagaaaggcg gacaggtatc cggtaagcgg cagggtcgga | 2400 |
| acaggagagc gcacgaggga gcttccaggg ggaaacgcct ggtatcttta tagtcctgtc | 2460 |
| gggtttcgcc acctctgact tgagcgtcga ttttgtgat gctcgtcagg ggggcggagc | 2520 |
| ctatggaaaa acgccagcaa cgcggccttt tacggttcc tggccttttg ctggccttt | 2580 |
| gctcacatgt tctttcctgc gttatcccct gattctgtgg ataaccgtat taccgccttt | 2640 |
| gagtgagctg ataccgctcg ccgcagccga acgaccgagc gcagcgagtc agtgagcgag | 2700 |

-continued

```
gaagcggaag agcgcctgat gcggtatttt ctccttacgc atctgtgcgg tatttcacac    2760
cgcatatggt gcactctcag tacaatctgc tctgatgccg catagttaag ccagtatata    2820
cactccgcta tcgctacgtg actgggtcat ggctgcgccc cgacacccgc caacacccgc    2880
tgacgcgccc tgacgggctt gtctgctccc ggcatccgct tacagacaag ctgtgaccgt    2940
ctccgggagc tgcatgtgtc agaggttttc accgtcatca ccgaaacgcg cgaggcccag    3000
ctggcttatc gaaattaata cgactcacta tagggagacc caagcttgca tgcctgcagg    3060
tcgactctag aggatcctgc gcgggacgtc ctttgtctac gtcccgtcgg cgctgaatcc    3120
cgcggacgac ccgtctcggg gccgtttggg actctaccgt cccttcttc atctgccgtt     3180 ccggccgacc acgggcgca cctctcttta cgcggtctcc ccgtctgtgc cttctcatct     3240
gccggtccgt gtgcacttcg cttcacctct gcacgtcgca tggagaccac cgtgaacgcc    3300
caccaggtct tgcccaaggt cttacataag aggactcttg gactctcagc gatgtcaacg    3360
accgaccttg aggcatactt caaagactgt ttgtttaagg actgggagga gttgggggag    3420
gagattaggt taaaggtctt tgtactagga ggctgtaggc ataaattggt ctgttcacca    3480
gcaccatgca acttttttcac ctctgcctaa tcatctcatg ttcatgtcct actgttcaag   3540
cctccaagct gtgccttggg tggctttggg gcatggacat tgacccgtat aaagaatttg    3600
gagcttctgt ggagttactc tctttttttgc cttctgactt ctttccttct attcgagatc   3660
tcctcgacac cgcctcagct ctatatcggg aggcctgcgg ccgctcgagt taactagtcg    3720
cgatgcatcg atgatcaccc gggccatggc tgctagggtg tgctgccaac tggatcctgc    3780
gcgggacgtc ctttgtctac gtcccgtcgg cgctgaatcc cgcggacgac ccgtctcggg    3840
gccgtttggg actctaccgt cccttcttc atctgccgtt ccggccgacc acgggcgca     3900 cctctcttta cgcggtctcc ccgtctgtgc cttctcatct gccggtccgt gtgcacttcg    3960
cttcacctct gcacgtcgca tggagaccac cgtgaacgcc caccaggtct tgcccaaggt    4020
cttacataag aggactcttg gactctcagc gatgtcaacg accgaccttg aggcatactt    4080
caaagactgt ttgtttaagg actgggagga gttgggggag gagattaggt taaaggtctt    4140
tgtactagga ggctgtaggc ataaattggt ctgttcacca gcaccatgca acttttttcac   4200 ctctgcctaa tcatctcatg ttcatgtcct actgttcaag cctccaagct gtgccttggg    4260
tggctttggg gcatggacat tgacccgtat aaagaatttg gagcttctgt ggagttactc    4320 tctttttttgc cttctgactt ctttccttct attcgagatc tcctcgacac cgcctcagct   4380
ctatatcggg aggggtacc gagctcgaat tccgtgtatt c                          4421
```